United States Patent [19]

Abu-Shumays et al.

[11] 4,437,812

[45] Mar. 20, 1984

[54] SINGLE-PUMP MULTIPLE STROKE PROPORTIONING FOR GRADIENT ELUTION LIQUID CHROMATOGRAPHY

[75] Inventors: Ahmad Abu-Shumays, Los Altos; John C. Helmer, Menlo Park; Stephen J. Luchetti, Berkeley, all of Calif.

[73] Assignee: Varian Associates, Inc., Palo Alto, Calif.

[21] Appl. No.: 305,426

[22] Filed: Sep. 25, 1981

Related U.S. Application Data

[63] Continuation of Ser. No. 796,782, May 13, 1977, abandoned.

[51] Int. Cl.³ .................. F04B 49/00; B67D 5/46
[52] U.S. Cl. ..................... 417/53; 417/442; 210/198.2; 222/1; 221/129
[58] Field of Search ............... 222/1, 14, 71, 135, 222/136, 144.5, 129; 210/198.2, 101; 417/53, 442, 473, 505, 427

[56] References Cited

U.S. PATENT DOCUMENTS

| | | | |
|---|---|---|---|
| 3,136,616 | 6/1964 | Thompson | 417/473 |
| 3,771,490 | 11/1973 | Kinney et al. | 222/136 |
| 3,893,591 | 7/1975 | Hocksmith | 222/1 |
| 3,985,019 | 10/1976 | Boehme et al. | 73/61.1 C |
| 3,990,610 | 11/1976 | Boer | 222/136 |
| 4,045,343 | 8/1977 | Achener | 73/61.1 C |
| 4,060,178 | 11/1977 | Miller | 222/14 |

*Primary Examiner*—William L. Freeh
*Attorney, Agent, or Firm*—Stanley Z. Cole; Gerald M. Fisher

[57] ABSTRACT

In a high-performance, high-pressure liquid chromatography system, gradient elution of solvent components from a plurality of component reservoirs can be accomplished according to a programmed temporally variable ratio by a single reciprocating pump. The pumping cycle comprises a plurality of fill strokes with intervening pumping strokes. During one of the fill strokes of the cycle, a proportioned mixture of solvent components is admitted to the pump chamber from the respective reservoirs by means of proportioning valves. During each of the other fill strokes of the cycle, only a single solvent component is admitted to the pump chamber. Consequently, a relatively low concentration of a particular component can be delivered by the pump with precision over a complete pumping cycle, although a comparatively higher and therefore more accurately measurable concentration of that component is admitted to the pump chamber during any given fill stroke. The opening and closing of the proportioning valves during the component proportioning fill stroke is sequenced to minimize deviations of the relative concentrations from the programmed concentration ratio. Proper sequencing of the proportioning valves reduces inaccuracies that would otherwise tend to occur, especially at the upper and lower concentration limits, due to effects related to the compressibility of residual solvent remaining in the pump chamber at the end of each pumping stroke.

14 Claims, 7 Drawing Figures

SINGLE-PUMP MULTIPLE STROKE PROPORTIONING FOR GRADIENT ELUTION LIQUID CHROMATOGRAPHY

This application is a continuation of application Ser. No. 796,782, filed May 13, 1977, now abandoned.

BACKGROUND OF THE INVENTION

This invention is a further development in high-performance, high-pressure liquid chromatography, and relates generally to the solvent supply system for use in gradient elution liquid chromatography. In particular, this invention is concerned with the use of a single reciprocating pump for gradient elution liquid chromatography, and provides a technique for minimizing inaccuracies in the relative concentrations of the solvent components pumped from a plurality of reservoirs for passage through a chromatographic column.

Most prior art systems for gradient elution liquid chromatography used a separate pump for each of the components of the solvent mixture. The relative flow rates at which the pumps delivered their respective components to a mixing chamber determined the relative proportion of each component in the mixture. Typically, the pumping flow rates for the individual components were programmed to very temporally according to a desired schedule. In a two-component system for example, the concentration of the component supplied to the mixing chamber by one pump might be programmed to vary with time from 0% to 100% at a linear rate of 5% per minute. Pumps of various kinds were used, including reciprocating pumps or constant-displacement pumps of the syringe type.

Recently, single-pump systems have been developed for two-component gradient elution applications, with fast-acting valves serving to admit the two components to the pump chamber during the fill stroke according to a desired concentration ratio. Thus, in a two-component system, the duration of the fill stroke was shared between two proportioning valves according to the desired concentration ratio of the two components in the outflow from the pump. If a 20% concentration of one component in the outflow solvent mixture were desired, the corresponding valve admitting that component into the pump chamber would be opened for 20% of the duration of the fill stroke, while the other proportioning valve would be opened for the remaining 80% of the fill stroke duration. This sequencing of the opening and closing of the proportioning valves was repeated during successive fill strokes. The outflow from the pump was typically passed into a mixing chamber, wherein the mixture would homogenize.

Single-pump systems for use in gradient elution chromatography are described in U.S. Pat. Nos. 3,985,019 and 3,985,021, which have been assigned to the assignee of the present patent application. The liquid chromatography system described in these patents, the disclosures of which are incorporated herein by reference, includes the following: a chromatographic column; first and second reservoirs, each reservoir containing a particular solvent component to be introduced into the solvent mixture that serves as the mobile phase passing through the chromatographic column; reciprocating pumping means for causing the mobile phase to flow through the chromatographic column; motor means for driving the pumping means through successive pumping cycles, each pumping cycle comprising a fill stroke and a pumping stroke; first and second solenoid-actuated proportioning valves positioned at the low-pressure end of the pumping means, whereby components from the first and second reservoirs, respectively, are admitted into the pumping means according to a desired ratio; gradient setting means, whereby a temporally varying ratio for the components entering the pumping means from the first and second reservoirs can be preselected for a desired time interval; and means responsive to the gradient setting means, whereby the first and second proportioning valves can be actuated in complementary fashion with respect to their opening and closing so that the first valve is open while the second valve is closed during one portion of the fill stroke, and the first valve is closed while the second valve is open during another portion of the same fill stroke. Thus, it was known to the prior art to divide the fill stroke of a reciprocating pump into a first portion during which a first solvent component is pumped from a first reservoir, and a second portion during which a second solvent component is pumped from a second reservoir, according to a preselected temporally varying ratio as determined by a gradient setting means.

With single-pump gradient elution systems known to the prior art, in order to maintain the required flow rate for the solvent mixture through the chromatographic column, the reciprocating piston of the pumping means was required to travel back and forth at a relatively high velocity. The time duration of the fill stroke was independent of the speed of the reciprocating piston during the pumping stroke, and was typically selected to be approximately 0.2 second.

For convenience hereinafter, the solvent in the first reservoir shall be referred to as "component A," and the solvent in the second reservoir shall be referred to as "component B." At a time during the gradient elution program when substantially pure component A is required, i.e., when the concentration level of component B in the mobile phase outflow from the pumping means is substantially 0%, the proportioning valve associated with the second reservoir (hereinafter referred to as valve B) must remain closed throughout the 0.2-second duration of the fill stroke. As the temporally varying gradient elution changes to require a 1% concentration of component B, valve B is required to be open for approximately 0.002-second during the fill stroke, while the other valve (hereinafter referred to as valve A) remains open for the remainder of the fill stroke. Such precise time resolution is required in high-precision liquid chromatography, but is difficult to provide with mechanical proportioning valves. Thus, single-pump gradient elution systems known to the prior art tend to exhibit relatively large errors in gradient concentrations near the 0% and 100% concentration levels because of the inability of mechanical proportioning valves to provide the required time resolution.

Another factor that adversely affected the performance of single-pump gradient elution systems known to the prior art was the presence of finite residual volumes of solvent liquid within the pumping means after completion of the pumping stroke. Such residual liquid was compressed during the pumping stroke; and as the piston began to withdraw from the pump chamber in preparation for the next fill stroke, this compressed liquid tended to spit back into the particular component reservoir for which the corresponding proportioning valve was open. This spit-back effect was attributable to a lower pressure in the component reservoir than in the pump chamber. Because of this spit-back effect, there was an uncertainty as to the exact instant in time at which the pump chamber would begin to fill from the reservoir. Since the entire fill stroke was on the order of only 0.2-second, and since the gradient elution program might require that the proportioning valve for the particular reservoir be open for only a very small portion (e.g., 1%) of the duration of the fill stroke, this uncertainty in the starting time for the admission of solvent from a particular reservoir into the pump chamber often resulted in very significant inaccuracies in the concentration ratio for the components of the solvent mixture, particularly near the 0% and 100% concentration levels.

Another factor that adversely affected the performance of single-pump gradient elution systems known to the prior art was the "spit-forward" phenomenon, which occurred when the pressure in a reservoir for which the corresponding proportioning valve was open was greater than the pressure in the pump chamber. In that situation, the observe of the spit-back phenomenon would occur, i.e., the component in the open reservoir would be sucked into the pump chamber. This suction of reservoir liquid into the pump chamber prior to the onset of the scheduled proportioning according to the gradient setting means often resulted in significant inaccuracies in the concentration ratio of the solvent components, particularly near the 0% and 100% concentration levels.

SUMMARY OF THE INVENTION

It is a principal object of this invention to provide a high-performance, high-pressure liquid chromatography system using a single reciprocating pump for gradient elution of solvent components from a plurality of reservoirs, wherein precise gradient proportioning of the components can be provided particularly near the upper and lower concentration limits for any particular component.

It is likewise an object of this invention to provide a high-performance, high-pressure liquid chromatography system employing a single reciprocating pump for gradient elution of components from a plurality of reservoirs, wherein timing uncertainties in the precise beginning of a fill stroke due to pressure differences between the component in a reservoir and the residual liquid in the pump chamber do not result in significant differences between the relative concentrations of the components in the outflow mixture from the pump and the programmed ratio for these concentrations.

It is also an object of this invention to provide a high-performance, high-pressure liquid chromatography system employing a single reciprocating pump for gradient elution of components from a plurality of reservoirs, with proportioning valves being used to admit the distinct components according to a programmed ratio from particular reservoirs into the pump chamber during a given fill stroke, wherein the sequence of opening and closing of the proportioning valves during that fill stroke serves to minimize the effect of timing uncertainties with respect to the beginning of the fill stroke.

It is likewise an object of this invention to provide a high-performance, high-pressure liquid chromatography system employing a single reciprocating pump for gradient elution of components from a plurality of reservoirs where the pumping cycle comprises a plurality of fill strokes with intervening pumping strokes, with proportioning valves being used to admit the components according to a programmed ratio from particular reservoirs into the pump chamber during a given fill stroke, the concentration of any particular component in any given fill stroke being at a relatively high and accurately measurable value.

It is also an object of this invention to provide a technique for gradient elution in a chromatographic system using a single reciprocating pump, whereby a very low concentration of a particular solvent component can be delivered with precision by the pump over a pumping cycle that comprises a plurality of fill strokes, with the concentration of that particular component in a given fill stroke being relatively higher and more accurately measurable than its averaged concentration over the complete pumping cycle.

It is a further object of this invention to minimize the effect of the compressibility of a solvent liquid in introducing uncertainties with respect to the beginning of a fill stroke in a gradient elution system employing a single reciprocating pump.

Pursuant to the aspect of this invention pertaining to the sequencing of the operation of the proportioning valves, the valve sequencing operation is programmed so that compressed solvent remaining in the pump chamber after the end of a pumping stroke can spit back only into a reservoir other than one containing the solvent component for which a low percentage concentration is desired in the outflow mixture from the pump. Thus, where valves A and B can admit components A and B, respectively, into the pump chamber, in a situation in which a very low concentration of component B is desired, the proportioning valves are sequenced so that valve A is already open when the inlet valve to the pump chamber opens. In this way, the compressed solvent mixture, which consists principally of component A, can spit back only into the A reservoir line. Similarily, where a high percentage concentration of component B is to be pumped, valve B is programmed to be already open when the inlet valve to the pump chamber opens so that the compressed solvent mixture, which in this case would comprise mostly component B, can spit back only into the B reservoir line. In cases where intermediate percentages of the A and B components are desired, the sequencing of the operation of valves A and B is programmed among groups of fill strokes in order to offset the "spit-back" or "spit-forward" phenomena associated with the compressibility of the solvent liquid. Thus, for example, if nearly equal percentages of the A and B components are desired in the outflow from the pump, the sequencing of the opening and closing of valves A and B may be alternated on the proportioning fill strokes of successive pumping cycles, or on otherwise paired fill strokes. Such alternating of the sequence for opening and closing valves A and B on successive cycles causes any error that might arise from the compressibility of the solvent to be alternately positive and negative on successive pumping cycles, thereby minimizing the overall concentration error over a number of successive cycles.

Pursuant to the aspect of this invention wherein a complete pumping cycle comprises a plurality of fill strokes, the actual proportioning of the different components can be programmed to occur only during one of the fill strokes of the complete cycle. Thus, to provide a given desired low concentration for a particular component in the outflow from the pump over the complete pumping cycle, the concentration of that component admitted into the pump chamber during a single fill stroke can be greater than the concentration of that component in the pump outflow by an amount that is proportional to the total number of fill strokes in the complete pumping cycle. In a typical procedure, the complete pumping cycle might comprise four fill strokes, with proportioning of components A and B occurring only during one of the four strokes, and with the pump chamber being filled with all component A or all component B during each of the other three fill strokes.

The most general multiple-stroke pumping cycle comprises the combination of m fill strokes of the type wherein valve A is open when the inlet valve to the pump chamber starts to open (hereinafter referred to as the A-B type of stroke), followed by n strokes of the type wherein valve B is open when the inlet valve to the pump chamber starts to open (hereinafter referred to as the B-A type of stroke).

DESCRIPTION OF THE PREFERRED EMBODIMENT

Figure 1:
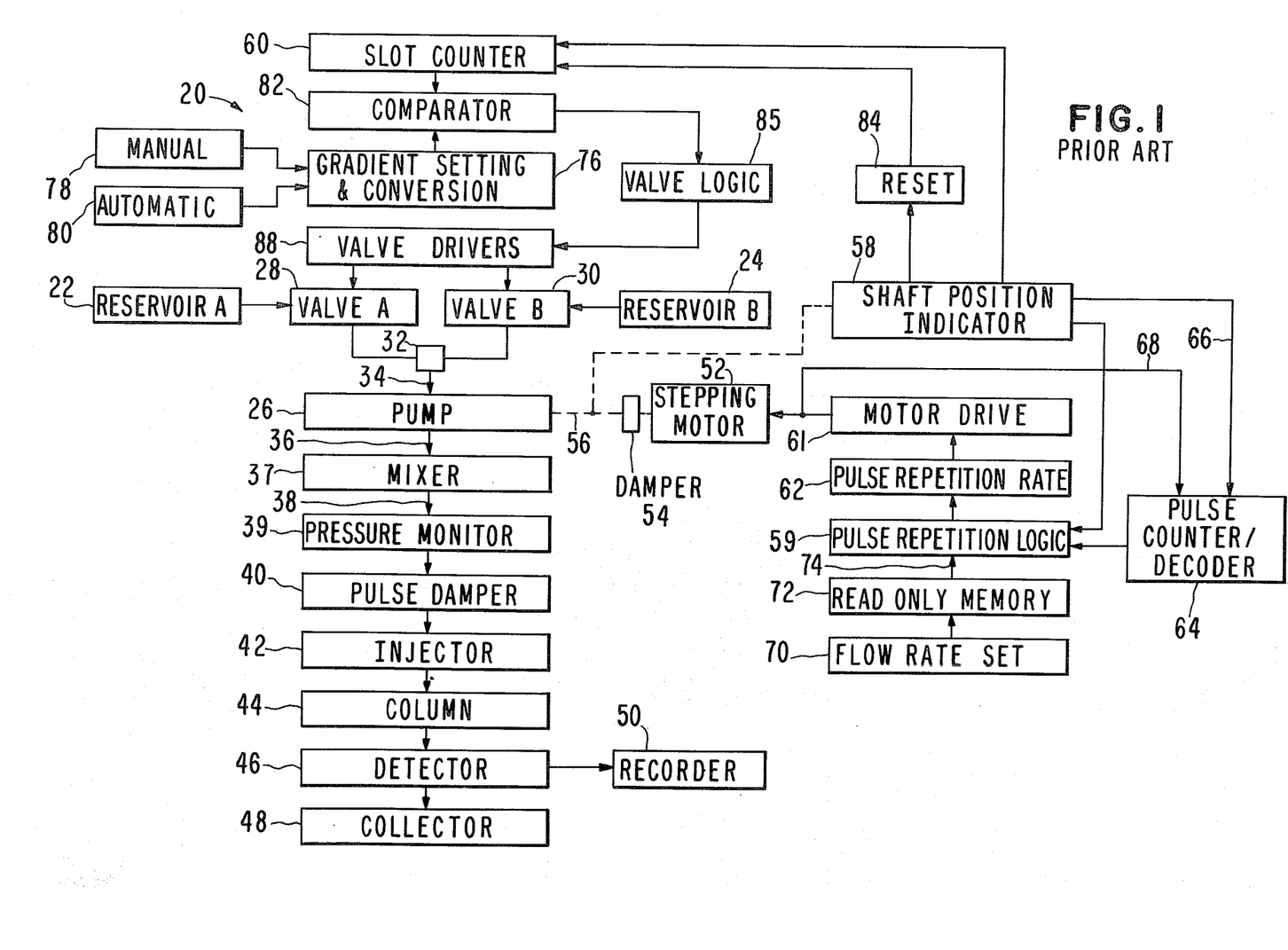
FIG. 1 is a simplified block diagram of a single-pump gradient elution liquid chromatography system known to the prior art.

The block diagram of FIG. 1 indicates the key elements of a gradient elution liquid chromatography system 20. The system 20, to the extent set forth in FIG. 1, is prior art and substantially corresponds to the chromatography system disclosed in the aforementioned U.S. Pat. Nos. 3,985,019 and 3,985,021, the disclosures of which are incorporated herein by reference. The system 20, as set forth in FIG. 1, illustrates a representative system to which the improvement that is the subject of the present invention pertains. It is to be understood, however, that the present invention is not limited to use with the system 20 set forth in FIG. 1, but may be used in any liquid chromatography system employing a single reciprocating pump together with a plurality of reservoirs from which distinct solvent components can be pumped to a chromatographic column according to a programmed gradient elution schedule.

Figure 2:
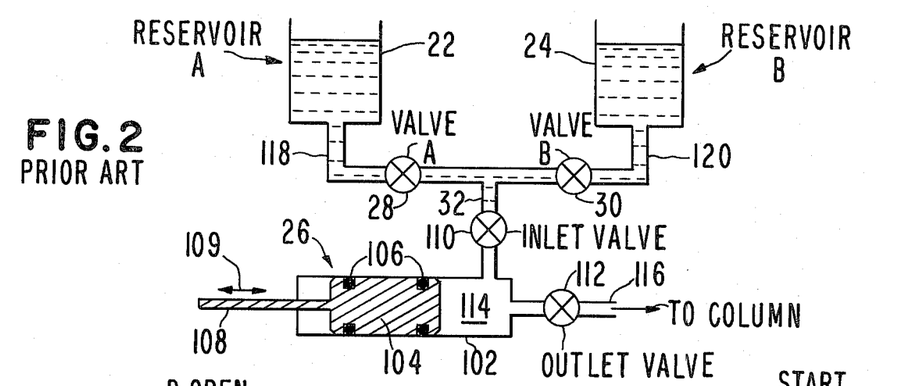
FIG. 2 is a schematic diagram illustrating portions of the prior art system of FIG. 1.

System 20 comprises two reservoirs 22 and 24, each of which contains a distinct solvent component, e.g., water in reservoir 22 and methanol in reservoir 24. For convenience hereinafter, reservoir 22 shall be designated as reservoir A, and reservoir 24 shall be designated as reservoir B. Likewise, the solvent component in reservoir 22 shall be designated as component A, and the solvent component in reservoir 24 shall be designated as component B. Each of the components A and B is furnished to a pump 26 by means of a solenoid valve. Thus, the component in reservoir 22 is furnished to the pump 26 via valve 28, and the component in reservoir 24 is furnished to the pump 26 via valve 30. Valve 28 shall hereinafter be designated as valve A, and valve 30 shall hereinafter be designated as valve B. Valves A and B serve to proportion the relative concentrations of components A and B in a mixing chamber 32 located upstream of the pump 26. The mixing chamber 32 may be a tee structure, as illustrated in FIG. 2. The solvent mixture is furnished to the pump 26 from the mixing chamber 32 via a line 34.

The output from the pump 26 may pass via a line 36 to a mixer 37 wherein the solvent mixture can be homogenized. The output from the mixer 37 passes via a line 38 to a pressure gauge or sensor 39. A safety device, such as a rupture disc not shown in FIG. 1, may be associated with the line 38 in order to prevent damage to the system from excessive pressure in the flow line. Typically, flow line pressures are of the order of 5,000 psi in gradient elution chromatography. The solvent mixture flow then proceeds through a pulse damper 40, which can be of the type described in U.S. Pat. No. 4,132,511 assigned to the assignee of the present patent application. The flow from the pulse damper 40 passes through a conventional injector device 42, and enters a chromatographic column 44. The output from the column 44 may be provided to a detector 46, and thence to a collector 48, in accordance with conventional chromatographic techniques. The detector 46 may be associated with a suitable recorder 50, as is known in the chromatographic art.

The pump 26 is driven by means of a stepping motor 52, which is per se conventional. A damper 54 may be associated with the stepping motor 52, as by being mounted on one end of the motor drive shaft, in a manner known to the prior art. The angular rotational velocity of the drive shaft of the stepping motor 52 is accurately controlled throughout a 360° rotational cycle, whereby the rotational velocity of a crankshaft 56 that is coupled thereto for driving the pump 26 may be accurately controlled.

A shaft position indicator 58 serves to indicate the rotational position of the pump crankshaft 56. The shaft position indicator 58 may comprise an encoding wheel with peripheral indicia such as slots marked thereon. The slots, or other indicia, may be read by a counter 60 during rotation of the pump crankshaft 56. Reference is made to the aforementioned U.S. patents for details of this counting arrangement.

A motor drive means 61 provides a series of electrical pulses to the stepping motor 52, which pulses cause the drive shaft of the stepping motor 52 to rotate in steps in accordance with the rate of pulse input. In order to enable the stepping motor 52 to be driven at differing average angular speeds depending upon the angular position of the pump crankshaft 56, the shaft position indicator 58 provides a reference signal to a pulse repetition logic device 59 whenever the pump crankshaft 56 reaches a given reference point in its angular rotation. Upon receiving this reference signal, the pulse repetition logic device 59 causes a pulse repetition rate device 62 to change the rate of pulse input to the stepping motor 52. Simultaneously, a pulse counter/decoder 64 is enabled via a control line 66, and begins to count successive pulses emanating from the motor drive means 61 via a line 68. The pulse counter/decoder 64, having effectively determined the angular position of the pump crankshaft 56, converts the counted pulses from the motor drive means 61 into a decoded signal that indicates to the pulse repetition rate device 62 the number of pulses per second that are appropriate for the then determined position of the pump crankshaft 56.

In the preferred embodiment of system 20, the output flow from the pump 26 may vary over a considerable range, such as, e.g., from 100 ml/hr up to a rate on the order of 1,000 ml/hr. In order to obtain the desired variation in pumping speed, a flow rate setting means 70 is provided, which may take the form of a single thumb switch. When a given flow rate is set, a preset programmed read-only memory means 72 provides a specified program for each portion of the cycle of operation of the pulse repetition logic device 59. The read-only memory means 72 is provided with a program appropriate for the desired flow rate, and instructs the pulse repetition logic device 59 via a line 74. The pulse repetition logic device 59 thereupon controls the pulse repetition rate device 62 accordingly.

In a typical mode for the operation of system 20, an elution of two solvent components is used. The ratio of the concentrations of the two components may in some instances be maintained at a relatively constant value. More commonly, however, the ratio between the concentrations of the two components must be varied during a test run, either by manual resetting of the ratio or by automatically controlled changes. A gradient setting and conversion means 76 is provided, which may have either a manually controlled input setting 78, or a programmed automatic gradient setting means 80, or both. Gradient programming is per se conventional, and details of devices for providing gradient programming are therefore not set forth herein.

The output from the gradient setting and conversion means 76, after having been converted to a suitable manipulatable form, is provided to a comparator 82. The numerical count from the slot counter 60 is reset once each cycle by a reset means 84 evry time a reference point is detected by the shaft position indicator 58 during rotation of the pump crankshaft 56.

When the output from the slot counter 60 proceeding via line 86 to the comparator 82 equals the converted value provided by the gradient setting and conversion means 76, an enabling signal is provided to a valve logic device 85, which activates valve drivers 88. The valve drivers 88 control the opening and closing of the valves 28 and 30, which operate in substantially complimentary fashion, i.e., one of these valves is open when the other is closed. By this arrangement, which is known to the prior art, one of the valves 28 and 30 can be open throughout a portion of the fill stroke for the pump 26, while the other of these valves remains closed; and for the remainder of the fill stroke, the obverse is true, i.e., the other of these valves is open while the first valve is closed. Thus, direct proportioning of the solvent components can be provided by deriving control signals for operating the valve drivers 88 in accordance with the angular position of the pump crankshaft 56. These control signals can be used to open and close the valves A and B in an appropriate manner so that the duration of a given fill stroke for the pump 26 can be shared between the entry of component A and the entry of component B into the tee structure 32. A more detailed discussion of the solvent proportioning that can be provided by complimentary operation of the valves A and B during a pump fill stroke is given in the aforementioned patents.

FIG. 2 provides a schematic depiction of certain portions of FIG. 1 that are pertinent to the present invention. The elements illustrated in FIG. 2, which are represented in block form in FIG. 1, are identified in both figures by the same reference numbers. In FIG. 2, the pump 26 is shown as comprising a simple reciprocating device, i.e., a cylinder 102 in which a piston 104 provided with piston rings 106 reciprocates in the directions indicated by the reference number 109 in response to the motion of a drive rod 108. The drive rod 108 is actuated by a suitable drive train in response to movement of the pump crankshaft 56 coupled to the drive shaft of the stepping motor 52. An inlet valve 110 is positioned between the tee structure 32 and the chamber 114 of the pump 26. Outflow from the pump chamber 114 passes to a chromatographic column via outlet line 116. The outflow to the line 116 is controlled by an outlet valve 112. The depiction in FIG. 2 is highly schematic. An actual device, which operates in accordance with the schematic depiction of FIG. 2, is described in greater detail in the aforementioned U.S. Pat. Nos. 3,985,019 and 3,985,021.

Figure 3:
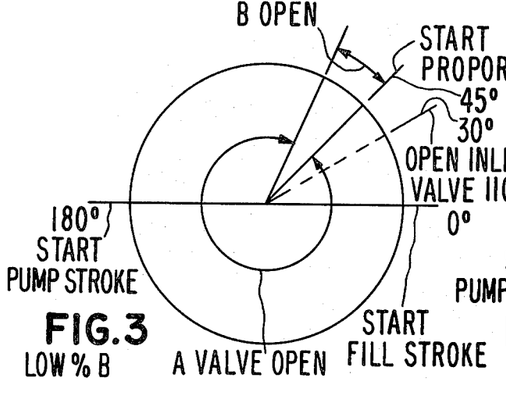
FIG. 3 is a schematic diagram illustrating a preferred proportioning valve sequence for a two-component gradient elution system according to the present invention, whereby a solvent mixture having relatively low percentage concentration of a particular component can be provided.
Figure 4:
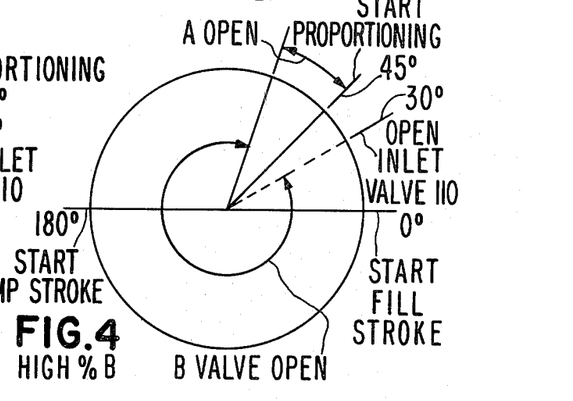
FIG. 4 is a schematic diagram similar to FIG. 3 illustrating a preferred proportioning valve sequence for the same system as in FIG. 2, whereby a relatively high concentration percentage of the same particular component can be provided.

Pursuant to one aspect of this invention, FIG. 3 and FIG. 4 provide schematic representations of proportioning valve sequences for use in gradient elution chromatography systems of the kind illustrated in FIG. 1 and FIG. 2. The proportioning valve sequencing technique of this invention for admitting distinct solvent components into a pumping means according to a programmed ratio is most advantageously employed where the solvent mixture to be advanced to the chromatographic column comprises only a very low proportion of the particular component.

FIG. 3 illustrates a proportioning valve sequence according to this invention for the two-reservoir system shown in FIG. 2, for use when a relatively low percentage concentration of component B is desired in the solvent mixture to be pumped to the chromatographic column. In FIG. 3, the states of the valves A and B, i.e., whether the valves are open or closed, are represented as a function of the position of the pump crankshaft 56. Each rotation of the crankshaft 56 results in a complete back and forth reciprocation of the piston 104 within the cylinder 102. (The valve sequencing operation depicted in FIG. 3 is similar to that represented by the timing diagrams of FIG. 23 of the aforementioned U.S. Pat. No. 3,985,019. Details of enabling operations for opening and closing the valves A and B indicated in FIG. 3, i.e., the electro-mechanical actuation of valves A and B, are explained in U.S. Pat. No. 3,985,019, the disclosures of which have been incorporated herein by reference.)

In the sequence shown in FIG. 3, the 0° crankshaft rotational position represents the start of a pump fill stroke. Valve A is already open when the crankshaft 56 reaches the 30° rotational position, at which point the inlet valve 110 opens. In operation, some of the compressed residual solvent mixture that remains in the pump chamber 114 and in the connecting lines to the inlet valve 110 and to the outlet valve 112, which was not ejected during the preceding pumping stroke, and which consists primarily of component A, is spit back into the line 118 leading to reservoir A. When the crankshaft 56 reaches the 45° shaft rotational position, valve B is thereupon opened, and valve A is closed in order to effect the desired proportioning between components A and B.

FIG. 4 shows a similar proportioning valve sequence according to this invention, which is suitable for use when a relatively high percentage concentration of component B is desired in the solvent mixture to be pumped to the chromatographic column. In the sequence shown in FIG. 4, valve B is already open when the crankshaft 56 reaches the 30° shaft rotational position, at which point the inlet valve 110 opens. Consequently, the compressed residual solvent mixture present in the pump chamber 114 and in the connecting lines to the inlet valve 110 and to the outlet valve 112, and which consists primarily of component B, is spit back into the line 120 leading to reservoir B. Subsequently, valve A is opened and valve B is closed at the 45° shaft rotational position in order to effect the desired proportioning of the solvents A and B.

The proportioning valve sequences shown in FIG. 3 and FIG. 4 are advantageous where the pump 26 is operated as in the prior art, i.e., in the mode in which solvent proportioning is effected during each successive fill stroke. When proportioning is effected during each fill stroke, the sequence shown in FIG. 3 is preferred when the concentration of component B in the mixture being pumped to the chromatographic column is in the range from 0% to 25%. The sequence shown in FIG. 4 is preferred when the concentration of component B in the mixture being pumped to the chromatographic column is in the range from 75% to 100%. At intermediate values for the concentration of component B in the mixture being pumped to the chromatographic column, i.e., when the concentration of component B is in the range from 25% to 75%, the valve sequences shown in FIG. 3 and FIG. 4 are preferably alternated for consecutive fill strokes, whereby errors due to the compressibility of any residual solvent mixture remaining in the pump chamber 114 and in the lines to the inlet valve 110 and the outlet valve 112 after the end of each pumping stroke will be alternately positive and negative.

A prime objective of the valve sequencing technique shown in FIG. 3 and FIG. 4 is to allow any spit-back that might occur to predominate in the direction of whichever reservoir contains the major component of the desired solvent mixture. Thus, if a multiple-stroke averaging technique is used, the sequences shown in FIG. 3 and FIG. 4 need not be maintained over the entirety of the respective percentage concentration ranges for which the sequences were indicated above to be preferred. In accordance with such a multiple-stroke averaging technique, each complete pumping cycle for a two-reservoir system comprises a plurality of fill strokes, with a pumping stroke intervening between every two consecutive fill strokes. The proportioning of the two components is programmed to occur only during one of the fill strokes in each complete pumping cycle.

More generally, according to this invention the proportioning of a plurality of components could be programmed to occur during less than all of the fill strokes of a pumping cycle. For example, with a four-stroke cycle, the valve sequencing illustrated in FIG. 3 would be used during only one of the four fill strokes of the cycle, thereby making possible an average B concentration in the range from 0% to 12% over the entire cycle. Thus, if an average B concentration of 12% over the entire cycle were desired, component B would be admitted into the pump chamber 114 during only one of the fill strokes of the cycle, and the ratio of the amount of component B to the amount of component A admitted during that fill stroke would be one to one. In other words, the concentration distribution of the solvent components in the pump during that one fill stroke would be half component B and half component A. For a smaller average B concentration over the entire cycle, component B would be admitted into the pump chamber 114 during only one fill stroke of the pumping cycle, but in a proportion less than one to one with respect to component A so that the resulting average B concentration over the entire cycle would be the desired value.

Similarly, with a five-stroke cycle, the valve sequencing illustrated in FIG. 3 would be used during only one of the five fill strokes of the cycle, thereby making possible an average B concentration in the range from 0% to 10% over the entire cycle. If an average B concentration of 10% over the entire cycle were desired, component B would be admitted into the pump chamber 114 during only one of the fill strokes of the cycle, and the ratio of the amount of component B to the amount of component A admitted during that one fill stroke would be one to one. For a smaller average B concentration, component B would be admitted into the pump chamber 114 during that fill stroke in a proportion less than one to one with respect to component A such that the desired average B concentration over the entire cycle would result.

The specific sequencing of the proportioning valves as indicated in FIG. 3 and FIG. 4 can be enabled by the techniques disclosed in the aforementioned U.S. Pat. Nos. 3,985,019 and 3,985,021. Implementation of these techniques to accomplish the proportioning valve sequencing disclosed herein lies within the scope of the present invention.

The present invention is also concerned with the problem encountered in the prior art in consequence of the fact that the response time for mechanical proportioning valves approaches the required time resolution for single-stroke proportioning, especially where the desired concentration percentage for a given component of the solvent mixture is near 0% or 100%. Pursuant to this aspect of the invention, it has been found that the error that would otherwise be introduced by the finite response time of mechanical proportioning valves can be reduced in proportion to the number of fill strokes that can be averaged over a complete pumping cycle. In the preferred mode of operation for a system according to this invention, a complete pumping cycle comprises a plurality of fill strokes with intervening pumping strokes, with preferably but a single fill stroke in the pumping cycle being used to achieve the desired percentage of the low-concentration component. For example, a concentration of 3% B can be provided by using three fill strokes of 0% B and one fill stroke of 12% B. Within a given fill stroke, a 12% B concentration can be provided with considerably greater accuracy than a 3% B concentration. Averaging the 12% B concentration for a single fill stroke over four consecutive fill strokes provides a 3% B concentration for the pumping cycle, which is more precise than could be obtained by attempting to proportion a 3% B concentration into each of the four consecutive fill strokes.

Figure 5:
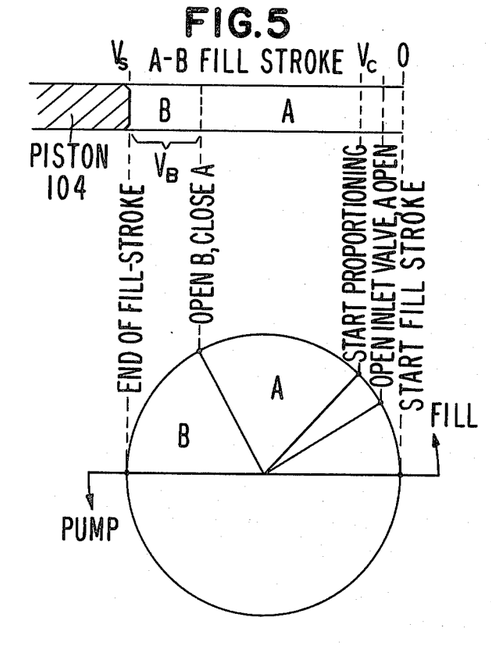
FIG. 5 is a schematic block diagram illustrating a generalized fill stroke of the A-B valve sequencing type.
Figure 6:
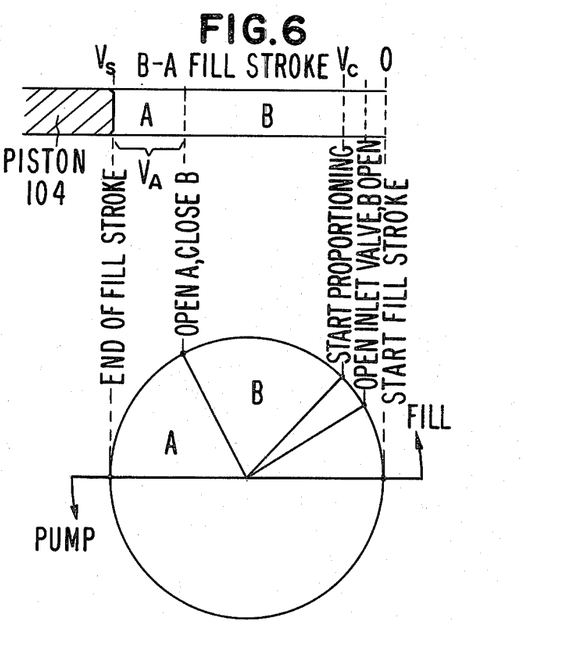
FIG. 6 is a schematic block diagram illustrating a generalized fill stroke of the B-A valve sequencing type.

FIG. 5 and FIG. 6 illustrate generalized fill strokes according to the present invention for providing gradient elution of components A and B according to a generalized program. The parameters used in FIG. 5 and FIG. 6 are defined as follows:

$V_c$=compression volume (i.e., residual volume in the pump at the start of proportioning);

$V_s$=total stroke volume at the end of proportioning (i.e., at the beginning of the pumping stroke);

$V_s-V_c$=partitioning volume (i.e., the volume delivered during the pumping stroke);

$V_B$=volume of component B admitted into the pump during the A-B stroke; and $V_A$=volume of component A admitted into the pump during the B-A stroke.

It is noted that $V_s-V_c$ is equivalent to the "fill volume" of the pump, i.e., the net volume of liquid actually drawn into the pump during one fill stroke. This "fill volume" is less than the total stroke volume $V_s$ because of the residual liquid remaining in the pump chamber at the end of a pumping stroke.

In a stroke of the A-B type, as shown in FIG. 5, valve A is programmed to be already open at the time when the inlet valve 110 is being opened. In a stroke of the B-A type, as shown in FIG. 6, valve B is programmed to be already open at the time when the inlet valve 110 is being opened.

The most general multiple-stroke cycle comprises a combination of m strokes of the A-B type, and n strokes of the B-A type. For purposes of generality, $V_B$ is assumed to have a different value for each of the m strokes of the A-B type. Similarly, $V_A$ is assumed to have a different value for each of the n strokes of the B-A type. It is assumed that the mixer 37 averages the m+n strokes so as to deliver an average concentration of components A and B to the chromatographic column.

For a complete cycle comprising m+n strokes, the volume of component B admitted to the pump chamber 114 is the sum $$\sum_{i=1}^{m} V_{Bi}$$

during the A-B strokes and $$\left[ n(V_s - V_c) - \sum_{j=1}^{n} V_{Aj} \right]$$

during the B-A strokes. The total volume of the solvent mixture transmitted by the pump during a complete pumping cycle is $(m+n)(V_s-V_c)$. The average concentration $C_B$ for component B pumped during a complete cycle can be expressed as follows:

$$\overline{C}_B = \frac{\sum_{i=1}^{m} V_{Bi} + n(V_s - V_c) - \sum_{j=1}^{n} V_{Aj}}{(m+n)(V_s - V_c)} \quad \text{Eq.(1)}$$

Rearranging the right-hand side, Eq. (1) may be expressed as:

$$\overline{C}_B = \frac{\sum_{i=1}^{m} V_{Bi} - \sum_{j=1}^{n} V_{Aj}}{(m+n)(V_s - V_c)} + \frac{n}{(m+n)} \quad \text{Eq.(2)}$$

Eq. (2) shows that, independently of the value $V_c$, the average B concentration is equal to m/(m+m) if the condition $$\sum_{i=1}^{m} V_{Bi} = \sum_{j=1}^{n} V_{Aj}$$

is satisfied. Thus, a series of match-points between the programmed ratio for components A and B, as determined by the gradient setting and conversion means 76 shown in FIG. 1, and the B concentration can be provided corresponding to the values m/(m+m). If a 4-stroke pumping cycle is considered, m+n=4; and match-points occur at $\overline{C}_B$ values corresponding to m/(m+m)=0/4, ¼, 2/4, ¾, 4/4, which is to say that match-points occur at the 0%, 25%, 50%, 75%, and 100% concentrations for component B. Similarly, for a 5-stroke pumping cycle, match-points occur at the 0%, 20%, 40%, 60%, 80% and 100% concentrations for component B. Program accuracy and the precision between match-points depend upon the parameters defined in the first term on the right-hand side Eq. (2).

Figure 7:
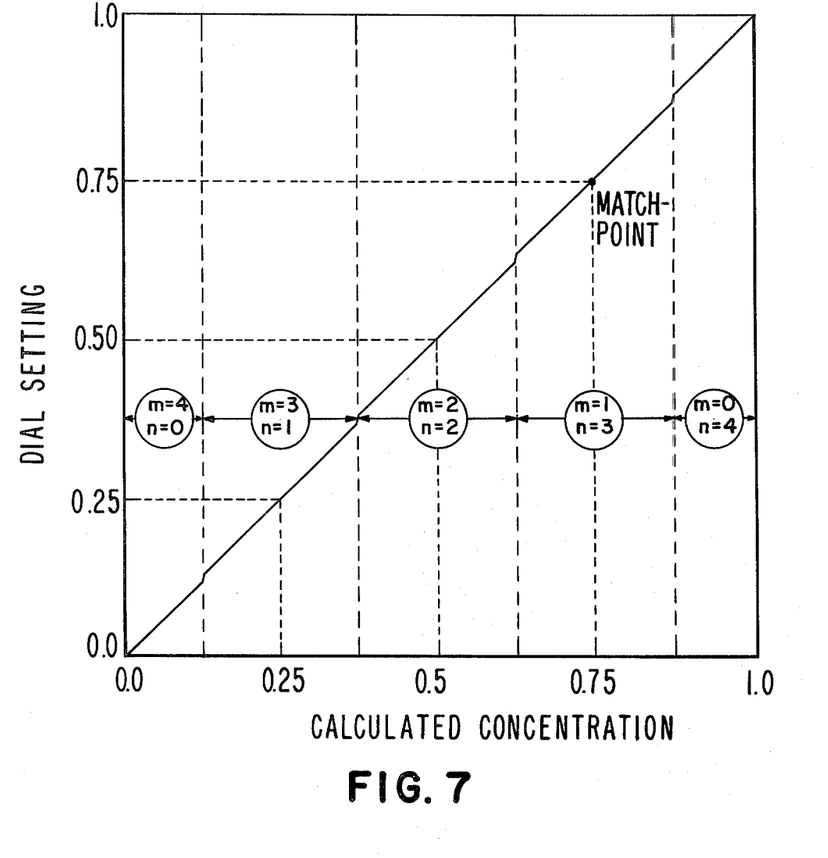
FIG. 7 is a graphic depiction of a representative 5-segment gradient elution program covering the 0% to 100% concentration range, and utilizing a 4-stroke fill cycle according to this invention.

FIG. 7 illustrates a simple 5-segment fill stroke program based upon a 4-stroke pumping cycle, which covers the complete 0% to 100% B concentration range. Each segment of the fill stroke includes a concentration match-point, and covers a concentration range that extends half-way to the neighboring match-points in either direction. All program segments have a common feature: viz, only one of the four strokes is used to generate concentration changes and the other three strokes remain unchanged during a pumping cycle. Furthermore, changes in the concentration-controlling fill-stroke are essentially similar for all program segments.

With reference to FIG. 7, the first segment covers the concentration range $0 \leq \overline{C}_B \leq 0.12$. The initial concentration $\overline{C}_B=0$ is a match-point. Four A-B strokes and no B-A strokes are used in a pumping cycle for which $\overline{C}_B=0$, i.e., m=4 and n=0. Thus, the program starts with all $V_{Bi}=0$ corresponding to $\overline{C}_B=0$. Only a single stroke is used to generate $\overline{C}_B$. In accordance with Eq. (2), $\overline{C}_B=V_{B4}/4(V_s-V_c)$. Thus, if $V_{B4}$ is stepped in increments of 0.04 $(V_s-V_c)$, the program will be able to provide twelve different concentrations between $0 \leq C \leq 0.12$, with a 1% increment. This program segments ends with $V_{B4}=0.48(V_s-V_c)$, which corresponds to $\overline{C}_B=0.12$.

The second segment of the program covers the concentration range $0.13 \leq C \leq 0.37$, and utilizes three A-B strokes and one B-A stroke, i.e., m=3 and n=1. This program starts with $V_{Bi}=0$ and $V_{A1}=0.48(V_s-V_c)$. In accordance with Eq. (2), for the second segment $\overline{C}_B = -V_{A1}/4(V_s-V_c) + ¼ = 0.13$.

For 1% B concentration steps, $V_{A1}$ decreases in increments of 0.04 $(V_s-V_c)$. There is a match point for $V_{A1}=0$, corresponding to $\overline{C}_B=0.25$. At this match point, the B-A stroke is 100% B. The program resumes by incrementing $V_{B1}$ in steps of 0.04 $(V_s-V_c)$, while maintaining $V_{Bi}=0$ for i=2, and $V_{Aj}=0$ for j=1. For these values of $V_{Bi}$ and $V_{Aj}$, Eq.(2) becomes $\overline{C}_B=V_{B3}/4(V_s-V_c)+¼$. This second program segment ends with $V_{B3}=0.48(V_s-V_c)$, which corresponds to $\overline{C}_B=0.37$.

The third program segment covers the concentration range $0.38 \leq \overline{C}_B \leq 0.62$, and utilizes two A-B strokes and two B-A strokes, i.e., m=2 and n=2. The center concentration $\overline{C}_B=0.5$ is a match-point. The program starts with $V_{Bi}=0$, $V_{A1}=0.48(V_s-V_c)$, and $V_{A2}=0$. For these values of $V_{Bi}$, $V_{A1}$, and $V_{A2}$, Eq.(2) becomes $\overline{C}_B=-V_{A1}/4(V_s-V_c)+½=0.38$. For 1% B concentration steps, $V_{A1}$ is reduced in increments of 0.04 $(V_s-V_c)$ until $V_{A1}=0$, at which point $\overline{C}_B=0.5$. At this center concentration, B-A strokes are 100% B. The program thereafter continues by incrementing $V_{B2}$ in 1% concentration steps ending with $V_{B2}=0.48$ $(V_s-V_c)$, at which point $\overline{C}_B=0.62$.

By an extension of the foregoing analysis, one A-B stroke and three B-A strokes are utilized for the fourth program segment, i.e., m=1 and n=3; and no A-B strokes and four B-A strokes are utilized for the fifth program segment, i.e., m=0 and n=4.

The expression for $\overline{C}_B$ as given by Eq.(2) consists of two terms. The second term, m/(m+m), is a numerical constant, which corresponds to a particular concentration match-point depending upon the particular values of m and n.

The first term, $$\frac{\sum\limits_{i=1}^{m} V_{Bi} - \sum\limits_{j=1}^{n} V_{Aj}}{(m+n)(V_s - V_c)}$$

corresponds to the difference between the dial setting selected for the gradient setting and conversion means 76 and the nearest match-point. In accordance with the gradient elution program used for practicing this invention with a four-stroke pumping cycle, the first term in Eq.(2) assumes a maximum value of 0.12, which corresponds to the end points of the particular program segment.

Two sources contribute to errors in component concentration, as can be seen by differentiating Eq.(2), $$\Delta \overline{C}_B = \frac{\Delta\left(\sum\limits_{i=1}^{m} V_{Bi} - \sum\limits_{j=1}^{n} V_{Aj}\right)}{(m+n)(V_s - V_c)} +$$

$$\frac{\sum\limits_{i=1}^{m} V_{Bi} - \sum\limits_{j=1}^{n} V_{Aj}}{(m+n)(V_s - V_c)} \cdot \frac{\Delta V_c}{(V_s - V_c)} \quad \text{Eq.(3)}$$

The first term of Eq.(3) shows that errors due to timing inaccuracies in the operation of the proportioning valves A and B contribute to errors in concentration. This first term in Eq.(3) can be reduced by increasing the number of strokes per cycle (m+n), and by further limiting the actual proportioning to a single stroke. The second term in Eq.(3) represents the uncertainty in $\Delta V_c$ resulting from decompression and spit-back of residual solvent at the end of a pumping stroke. This second term in Eq.(3) can also be reduced by increasing the number of strokes per cycle (m+n).

Experimental data obtained by the inventors indicates that for a gradient elution chromatography system according to this invention, the assumption of a 5% uncertainty in the proportioning stroke volume $(V_s-V_c)$ is conservative. Assuming a 5% uncertainty $\Delta V_c$ for the proportioning stroke volume $(V_s-V_c)$, the corresponding error in the average B concentration $\overline{C}_B$ is calculated as:

$$\Delta \overline{C}_B = \frac{\left(\sum\limits_{i=1}^{m} V_{Bi} - \sum\limits_{j=1}^{n} V_{Aj}\right)}{(m+n)(V_s - V_c)} \cdot \frac{\Delta V_c}{(V_s - V_c)}$$

$$= (\pm\, 0.12)(0.05)$$

$$= \pm\, 0.006, \text{ which is } \pm\, 0.6\%.$$

Thus, assuming a 5% uncertainty in the proportioning stroke volume, which experience indicates to be a conservative assumption, the maximum error in any program segment is only about 0.6%, which would occur at the segment ends.

In the above analysis, the order of the m strokes of the A-B type and the n strokes of the B-A type within any given pumping cycle is not specified. The order of these strokes can be advantageously specified to enhance the mixing of the A and B solvents during each complete cycle of m+n strokes. Thus, by alternating A-rich and B-rich strokes, the mixing requirements that would otherwise be imposed upon system components disposed downstream of the pump can be eased.

In the following example, the sequence of strokes is specified in order to provide the most advantageous mixing for components A and B. In this example, the pumping cycle comprises four fill strokes, with proportioning occurring only during one of these fill strokes. The remaining three fill strokes are some combination of "all A" strokes and "all B" strokes. Thus, throughout an entire pumping cycle, only one proportioning valve actuation occurs during a fill stroke. All other proportioning valve actuations occur prior to unproportioned fill strokes. The status of the proportioning valves A and B, i.e., whether open or closed, is indicated in the following
Table for each of the four fill-strokes.

TABLE

| Set. Pt.% B | Fill #1 | Fill #2 | Fill #3 | Fill #4 |
|---|---|---|---|---|
| 0% | A open | A open | A open | A open |
| 1%–12% | A open, then B for proportioning | A open | A open | A open |
| 13%–24% | B open, then A for proportioning | A open | A open | A open |
| 25% | B open | A open | A open | A open |
| 26%–37% | B open | A open | A open, then B for proportioning | A open |
| 38%–49% | B open | A open | B open, then A for proportioning | A open |
| 50% | B open | A open | B open | A open |
| 51%–62% | B open | A open, then B for proportioning | B open | A open |
| 63%–74% | B open | B open, then | B open | A open |

TABLE-continued

| Set. Pt.% B | Fill #1 | Fill #2 | Fill #3 | Fill #4 |
|---|---|---|---|---|
| | | A for proportioning | | |
| 75% | B open | B open | B open | A open |
| 76%-87% | B open | B open | B open | A open, then B for proportioning |
| 88%-99% | B open | B open | B open | B open, then A for proportioning |
| 100% | B open | B open | B open | B open |

Valve sequence switching in the above example occurs at the 12.5%, 37.5%, 62.5% and 87.5% concentrations for component B. For B concentration in the range from 0% to 12%, spit-back is always toward the A reservoir. In the B concentration range from 13% to 37%, spit-back is toward the B reservoir for one stroke and toward the A reservoir for three strokes. In the B concentration range from 38% to 62%, spit-back is toward the B reservoir for two strokes and toward the A reservoir for two strokes. In the B concentration range from 63% to 87%, spit-back is toward the B reservoir for three strokes and toward the A reservoir for one stroke. In the B concentration range from 88% to 100%, spit-back is always toward the B reservoir. To enhance mixing, the occurrence of the "all A" and "all B" strokes can be alternated. Thus, for example, at 50% B concentration, the program can provide that valve B be open during the first fill stroke, valve A be open during the second fill stroke, valve B be open during the third fill stroke, and valve A be open during the fourth fill stroke.

This invention has been set forth above in terms of specific embodiments. It will be understood from the disclosure, however, that numerous variations from these specific embodiments are possible to those skilled in the art, which variations lie within the scope of this invention. Accordingly, the invention is to be broadly construed, and is limited only by the following claims.

What is claimed is:

1. In a high pressure, high performance liquid chromatography system a method for providing gradient proportioning of a plurality of solvent components, said system comprising:
   a plurality of solvent reservoirs, each of said reservoirs containing a particular one of said solvent components,
   a single reciprocating pumping means,
   proportioning valves for admitting said solvent components into said pumping means from said reservoirs during fill strokes of said pumping means according to a programmed concentration distribution that may vary for different fill strokes, and
   a mixing structure into which said pumping means can deliver said plurality of solvent components, said gradient proportioning method comprising utilization of a pumping cycle that provides accurate proportioning near zero and one hunhundred percent concentration, said method includes a plurality of fill strokes, with a selected concentration distribution of more than one of said solvent components being permitted in said pumping means during less than all of the fill strokes of said pumping cycle and, during a said fill stroke in which a selected concentration is created, actuating the said proportioning valve for the higher concentration solvent prior to the activation of the said proportioning valve for the lower concentration solvent.

2. The method of claim 1 wherein a selected concentration distribution of more than one of said solvent components is permitted in said pumping means only during one fill stroke of said pumping cycle.

3. The method of claim 2 wherein a component comprising the major constituent of the desired outflow from said pumping means is permitted to enter said pumping means at the initiation of said one fill stroke during which the selected concentration distribution of more than one of said components is permitted in said pumping means.

4. The method of claim 3 wherein the number of fill strokes in said pumping cycle is four.

5. The method of claim 4 wherein said selected concentration distribution comprises a selected ratio of two solvent components.

6. The method of claim 3 wherein said component comprising the major constituent of the desired outflow from said pumping means comprises at least 75% of said outflow.

7. The method of claim 1 wherein a component comprising the major constituent of the desired outflow from said pumping means is permitted to enter said pumping means at the initiation of at least half of the fill strokes of said pumping cycle.

8. The method of claim 7 wherein the number of fill strokes in said pumping cycle is four.

9. The method of claim 7 wherein said component comprising the major constituent of the desired outflow from said pumping means comprises at least 75% of said outflow, and wherein said component is permitted to enter said pumping means at the initiation of at least three-quarters of the fill strokes of said pumping cycle.

10. The method of claim 8 wherein said component comprising the major constituent of the desired outflow from said pumping means comprises at least 88% of said outflow, and wherein said component is permitted to enter said pumping means at the initiation of all of the fill strokes of said pumping cycle.

11. A method for providing in a high pressure, high performance liquid chromatography system an accurately proportioned mixture of components in the liquid outflow from a single reciprocating pumping means near zero and one hundred percent concentrations, said components being admissible by proportioning valves from separate reservoirs into said pumping means according to a programmed concentration distribution that may vary for different fill strokes of said pumping means, said components being delivered by said pumping means to a single chamber wherein mixing of said components can occur, said outflow mixture having a specified concentration distribution for the components thereof over a pumping cycle for said reciprocating pumping means, said pumping cycle comprising a plurality of fill strokes for said pumping means, the method for providing said mixture of components comprising the admission of components into said pumping means during the fill strokes of said cycle in accordance with a program that provides for a characteristic concentration distribution for said components particular to each of said fill strokes, the characteristic concentration distribution particular to at least one of said fill strokes being different from the selected concentration distribution for said outflow mixture over said pumping cycle, during the fill stroke of said at least one fill stroke having a different characteristic concentration; the proportioning valve for the higher concentration solvent is actuated prior to actuation of the proportioning valve for the lower concentration solvent, the average value of the characteristic concentration distributions for all of the fill strokes of said cycle being substantially equal to the selected concentration distribution for said outflow mixture over said pumping cycle.

12. The method of claim 11 applied to a system for providing a mixture of two components designated respectively as component A and component B in the outflow from said pumping means, wherein component A can enter said pumping means when a valve A is open and component B can enter said pumping means when a valve B is open, valve A and valve B being operable in complementary fashion so that either one of said valves may be open only when the other of said valves is closed.

13. The method of claim 12 wherein said pumping cycle comprises m fill strokes of the A-B type in which valve A is already open at the initiation thereof so that component A can enter into the pumping means before component B, and n fill strokes of the B-A type in which valve B is already open at the initiation thereof so that component B can enter into the pumping means before component A.

14. The method of claim 13 wherein said program, in accordance with which the components A and B are admitted into said pumping means, can be determined by assigning integral values to m and n in the equation:

$$\overline{C}_B = \frac{\sum_{i=1}^{m} V_{Bi} - \sum_{j=1}^{n} V_{Aj}}{(m+n)(V_s - V_c)} + \frac{n}{(m+n)}$$

where the sum m+n equal the total number of fill strokes in said pumping cycle, and where:

$\overline{C}_B$ represents the average concentration for component B over a complete pumping cycle, $V_c$ represents the residual volume of liquid in the pumping means at the initiation of a fill stroke, $V_s$ represents the stroke volume at the initiation of a pumping stroke, $V_B$ represents the volume of component B admitted into the pumping means during an A-B type of stroke, and $V_A$ represents the volume of component A admitted into the pumping means during a B-A type of stroke.

* * * * *